United States Patent [19]
Soudant et al.

[11] Patent Number: 5,194,259
[45] Date of Patent: Mar. 16, 1993

[54] **SLIMMING COMPOSITION BASED ON *GINKGO BILOBA* AS AN ALPHA-2-BLOCKER**

[75] Inventors: Etienne Soudant, Fresnes; Jean-François Nadaud, Paris, both of France

[73] Assignee: L'Oreal, Paris, France

[21] Appl. No.: 798,329

[22] Filed: Nov. 27, 1991

[30] Foreign Application Priority Data

Nov. 28, 1990 [FR] France ............... 90 14864

[51] Int. Cl.$^5$ .......................... A61K 9/107
[52] U.S. Cl. .................. 424/401; 424/195.1
[58] Field of Search .................. 424/401, 195.1

[56] References Cited

U.S. PATENT DOCUMENTS

| | | | |
|---|---|---|---|
| 4,187,291 | 2/1980 | Marissal | 424/195.1 |
| 4,525,359 | 6/1985 | Greenway, III et al. | 514/653 |
| 4,588,724 | 5/1986 | Greenway, III et al. | 514/250 |
| 4,683,140 | 7/1987 | Kang | 424/195.1 |
| 4,684,522 | 8/1987 | Marissal et al. | 424/195.1 |
| 4,767,618 | 8/1988 | Grollier et al. | 424/195.1 |
| 4,795,638 | 1/1989 | Ayache et al. | 424/195.1 |
| 4,800,080 | 1/1989 | Grollier et al. | 424/195.1 |
| 4,981,688 | 1/1991 | Ayroles et al. | 424/195.1 |
| 5,043,323 | 8/1991 | Bombardelli et al. | 514/844 |
| 5,080,901 | 1/1992 | Hangay et al. | 424/195.1 |

FOREIGN PATENT DOCUMENTS 0120165 10/1984 European Pat. Off. .

*Primary Examiner*—Thurman K. Page
*Assistant Examiner*—Amy Hulina
*Attorney, Agent, or Firm*—Cushman, Darby & Cushman

[57] ABSTRACT

A cosmetic slimming composition for topical application to the skin contains in combination *Ginkgo biloba* as an alpha-2-blocker and at least one other alpha-2-blocker. This anti-cellulitis composition is capable of checking or stopping local fat accumulation and improving the esthetic appearance of the skin.

10 Claims, No Drawings

SLIMMING COMPOSITION BASED ON *GINKGO BILOBA* AS AN ALPHA-2-BLOCKER

The present invention relates to the use of ginkgo biloba as an alpha-2-blocker in combination with at least one other alpha-2-blocker in the preparation of a slimming composition intended for topical application as well as to such compositions.

It is known that the swelling of sub-cutaneous conjunctive tissue called cellulitis gives to the skin a "quilted" appearance. Cellulitis is constituted by the local accumulation of fat and water trapped in a gangue having more or less tight compartments.

Topical application of an anti-cellulitis agent is capable of checking local fat accumulation by a lipolytic action thereby improving the esthetic appearance of the skin.

Among the methods of stimulating lipolysis the most known and employed is that which consists in inhibiting phosphodiesterase in order to prevent or at least limit the degradation rate of cyclic AMP. In effect, phosphodiesterase destroys cyclic AMP by transforming it into 5' AMP thus rendering it ineffective to function as a lipolysis activator. Inhibiting phosphodiesterase activity increases the amount of cyclic AMP at the level of the adipocytes which stimulates lipolytic activity.

Among the various phosphodiesterase inhibitors which have been recommended as slimming agents mention can be made, in particular, of xanthic bases and more particularly caffeine.

However, there exist other methods for combatting against the local fat accumulation such as the blockage of the alpha-2 receptors at the surface of the adipocytes by products called alpha-2-blockers.

The alpha-2 receptors are normally stimulated by natural products of the body (the catecholamines) in order to increase the lipid content of these cells, for example in periods of diet or stress. By blocking this activity, the alpha-2-blockers thus prevent fat accumulation in the adipose tissue and favor at the same time the release of fats.

The known alpha-2-blockers (for example, yohimbine) have until now been employed orally for various purposes such as for treating obesity. On the other hand, Greenway and coll. (Clinical Therapeutics, 1987, Vol. 9, No. 6, pp. 663–669) have shown that creams based on yohimbine, applied to women who also were subjected to stringent caloric restrictions and physical exercise, had an indirect lipolytic activity. But yohimbine and the alpha-2-blockers of this type poorly penetrated the skin (Greenway and coll. were obliged to employ hot wrappings). Further, they exhibited secondary effects thereby prohibiting their use in cosmetics.

It has now been discovered in a quite unexpected manner that certain products whose use in cosmetics is already known have an alpha-2-blocking activity when they are present in significant amounts.

In effect, the applicants have noticed that these alpha-2-blockers act only beyond a certain concentration. It is for this reason that a certain number of products, already known in cosmetics, although they have perhaps an alpha-2-blocking potential, have not been recognized until now as having this characteristic.

Representative products having this alpha-2-blocking activity at a high concentration, include principally ginkgo biloba, ivy and escine.

The use of ginkgo biloba is already known in cosmetics and principally for its vasodilator activity which increases the caliber of vessels (usually blood vessels) by relaxation of the muscles.

At moderate concentration, the vasodilators such as ginkgo biloba are employed in cosmetic compositions, for example, to maintain a good amount of hydration of the skin (European patent No. 275,005).

However, ginkgo biloba has never been described as having lipolytic activity.

Although the discovery of the alpha-2-blocking activity of ginkgo biloba might suggest its use in a slimming composition, the applicants have noted that when it is the only active principle, high concentrations of this product, which are necessary to obtain the desired effect, runs the risk of a too high vasodilator activity which presents a disadvantage for slimming or anti-cellulitis compositions intended for topical application.

Moreover, there exists for this product some cosmetic composition formulation problems, since beyond a certain threshold, ginkgo biloba has a latent odor and color and is also considered difficultly soluble at high concentrations.

There is then a dual problem: on the one hand to retain a high concentration of the alpha-2-blocker in a cosmetic composition in order to maintain the stimulating effect of the desired lipolysis and, on the other hand, to limit the concentration of ginkgo biloba.

Among other products for which the applicants have demonstrated an alpha-2-blocking activity at high concentration, ivy and escine are also already known in cosmetics and in particular in slimming compositions.

Ivy has been employed in combination with extracts of meadow sweet, centella asiatica and laminaire (French patent No. 2.571,616), in combination with a hormone (French patent No. 2.571.616) or in combination with the extract of arnica and the extract of kola nut (French patent No. 2.499.405) or with a purine base and of fragon (French patent No. 2.554.344) or even in combination with a substance having rubefaction activity (French patent No. 2.573/306).

Escine is usually employed as a vasoactive compound in slimming compositions, in particular in combination with mucopolysaccharides with which it reinforces and accelerates the slimming activity without so much acting directly on the adipocyte, all while protecting the blood vessels (French patent No. 2.463.617, Belgium patent No. 888,136, French patent No.2.400.902 and French patent No. 2.356.427).

Principally, and as for ginkgo biloba, these two products are employed in cosmetics only on the basis of their functional characteristics other than alpha-2-blocking ability.

Although the disclosure of the alpha-2-blocking activity of ivy as well as escine and ginkgo biloba might suggest their use in a slimming composition as the sole active principle, the applicants have noted that at the high concentration necessary to obtain the desired effect, escine has a sticky effect and ivy poses color problems. These are two significant disadvantages as far as a cosmetic composition is concerned.

The present invention thus relates to the use of ginkgo biloba as an alpha-2-blocker, in combination with at least one other alpha-2-blocker in the preparation of a slimming composition intended for topical application.

In effect, the applicants have noted that the disadvantages linked to a formulation containing ginkgo biloba at high concentrations can be resolved or reduced by combining this product with another alpha-2-blocker, preferably escine and/or ivy, in a cosmetic composition while retaining an alpha-2-blocker concentration sufficient to act against cellulitis.

Moreover, since escine and ivy also exhibit a vasoconstrictive activity, the combination according to the invention permits to correct the undesirable vasodilator effect of ginkgo biloba.

Additionally, since solvents for these three products, identified above, are not the same, more alpha-2-blockers can be employed in a formulation containing two substances than when using only a single such product.

The solvent preferably employed for ginkgo biloba is diethylene glycol monoethylether and, in particular, the product sold under the trade name "TRANSCUTOL" by Gattefosse. For ivy and escine, water is preferably used as the solvent.

The expression "ginkgo biloba" is employed to mean extracts of the plant of the same name. According to the invention, the extracts preferably employed are those sold under the trade name "EXTRAIT STANDARD DE GINKGO BILOBA" by Beaufour, which are obtained by extraction in an acetone/water mixture starting with leaves, or those sold by Inverni under the trade name "EXTRAIT SEC à GINKGO BILOBA".

The expression "escine" is employed to mean the o isomer, as well as its salts and principally the sodium salt, escine being a horsechestnut extract.

The expression "ivy" is employed to mean extracts of Hedera haelix L. (or creeping ivy) containing saponins. These extracts can be prepared by any process permitting the removal of constituents such as proteins, lipids, glucides, mucilages and tannins. According to the invention, the extracts of ivy, which are preferably employed, are those sold by Inverni under the trade name "LIERRE GRIMPANT SAPONINES TOTALES" or "EXTRAIT DE LIERRE" sold by Gattefosse.

The combination according to the invention also permits the protection against the negative effect of stress. This results from the fact that stress causes a discharge of epinephrine (a natural catecholamine) having fattening effects. It is a question in particular of the femoral area of a woman's body, that is to say, the "culotte de cheval", i.e. saddle bags (P. Mauriege and Coll. European Journal of Clinical Investigation, 1987, Vol. 17, p. 156-165).

On account of this combination according to the invention, substances liberated by the human body during stress and which, without this combination, greatly inhibits lipolysis at the femoral area, there is an inverse effect, that is to say, this combination frees adipocytes of their fatty reserve. Moreover, in these femoral areas, the combination according to the invention has a greater thinning effect than the most drastic hypocaloric regimen since the purpose of alpha-2-receptors is to avoid, under these regimen conditions, the movement of adipose fat.

The combination of a regimen of this type with a topical application of the alpha-2-blocker combination according to the invention is all the same recommended and synergistic, since the regimen alone does not reduce the "culotte de cheval", i.e. saddle bags. A cream containing nonlipolytic active alpha-2-blockers has only a very little effect in this area. On the contrary, a cream containing lipolytic active alpha-2-blockers has some effect; nevertheless these effects are clearly reinforced when an exercise regimen is combined with a topical application of a composition based on alpha-2-blockers since the fatty acids, liberated by the composition, are employed as a source of energy for the body. The same synergistic effect exists between the exercise and the topical application of a cream based on alpha-2-blockers.

The total amount of alpha-2-blockers in the composition resulting from the combination according to the invention is generally greater than 0.03% and preferably between 0.05 and 20 percent by weight.

In a general manner, the slimming cosmetic compositions according to the invention contain ginkgo biloba at a weight concentration of 0.02 to 5 percent (expressed as dry matter) and, preferably from 0.05 to 2 percent. The other alpha-2-blocker is present at a concentration of 0.01 to 15 percent by weight. When this alpha-2-blocker is escine, it is present in an amount ranging from 0.05 to 4 percent and, preferably, from 0.1 to 2 percent. When this alpha-2-blocker is ivy, it is present in an amount ranging from 0.01 to 15 percent and, preferably from 0.05 to 5 percent.

According to a particular embodiment of the invention there can be added, to the combination according to the invention, other lipolytic compounds such as those acting at the level of phosphodiesterase, for example, xanthic bases such as caffeine or $\beta$-agonists such as adrenalin, its derivatives or analogs or other lipolytic compounds.

These compounds can be provided in various forms, in particular in anhydrous form such as, for example, an oil or balm, or even as oil-in-water or water-in-oil emulsions having the appearance of a cream or milk or in the form of emulsified or clear gels, hydroalcoholic or not, and also in the form of lipidic vesicles as well as in the form of transdermic systems.

When the compositions are provided in the form of an emulsion, the oil phase of the emulsions represents from 10 to 80 weight percent, the aqueous phase from 15 to 8 weight percent and the emulsifying agent from 2 to 30 weight percent, based on the total weight of the emulsion.

Representative emulsifying agents include, preferably, high molecular weight carboxyvinyl polymers and principally the product sold under the name "CARBOPOL 941" by Goodrich, as well as mixtures of nonionic emulsifiers and principally the product sold under the trade nam "PROTEGIN X" by Goldschmidt.

When the compositions are provided in the form of vesicles the active principles are encapsulated in vesicles based on ionic lipids (liposomes) or on nonionic lipids.

The compositions according to the invention can also contain various conventional ingredients such as, for example, surfactants, polymers, silicone oils, emollients, thickening agents, perfumes, dyes, sweetening agents, antioxidants or preservatives. As has been described above, they can also contain known lipolytic agents such as caffeine.

Representative silicone oils preferably employed are cyclopentadimethylsiloxane and principally the product sold under the name "VOLATIL SILICONE 7158" by Union Carbide, as well as alkyldimethicone copolyol and principally the product sold under the trade name "ABIL WE 09" by Goldschmidt.

Among the surfactants preferably employed are glycerine monostearate and principally the product sold under the name "ARLACEL 165" by Atlas, and as sorbitan monostearate oxyethylenated with 20 moles of ethylene oxide and principally the product sold under the name "TWEEN 60" by Atlas.

Among the emollients, there are preferably employed ethylene oxide polymers, glyceryl cocoate oxyethylenated with 7 moles of ethylene oxide and principally the product sold under the trade name "CETIOL HE" by Henkel, as well as a mixture of glycol stearate and polyethylene glycol (6 and 32 PEG) and principally the product sold under the trade name a "TEFOSE 63" by Gattefosse.

Representative thickening agents preferably used are silica derivatives such as pyrogenous colloidal silica and principally the product sold under the trade name "AEROSIL 200" by Degussa Ag, as well as crosslinked polyacrylic acid and principally the product sold under the trade name "CARBOPOL 940" by Goodrich.

The present invention also relates to a cosmetic treatment process to improve the esthetic appearance of a person, comprising applying to the skin a slimming composition such as defined above. Generally this treatment is carried out for a period of 6 to 8 weeks at a rate of one or two applications per day.

The slimming cosmetic compositions according to the invention can also be administered by ionophoresis.

There are now given, as an illustration and without any restrictive character, several examples of compositions according to the invention.

EXAMPLE 1

A slimming oil-in-water emulsion

| | |
|---|---|
| "VOLATILE SILICONE 7158" | 10.0 g |
| Perhydrosqualene | 18.0 g |
| Petrolatum oil | 5.0 g |
| Liquid lanolin | 4.0 g |
| "ARLACEL 165" | 6.0 g |
| "TWEEN 60" | 2.0 g |
| Cetyl alcohol | 1.2 g |
| Stearic acid | 2.5 g |
| Triethanolamine | 0.1 g |
| Preservative | 0.3 g |
| Antioxidant | 0.3 g |
| Caffeine | 1.0 g |
| Ginkgo biloba extract, sold by Beaufour | 0.5 g |
| Propylene glycol | 5.0 g |
| Escine acid, sold by Inverni | 0.5 g |
| Sodium hydroxide | 0.008 g |
| Demineralized water, sufficient amount for | 100.0 g |

EXAMPLE 2

A slimming oil-in-water emulsion

| | |
|---|---|
| Propylene glycol | 2.0 g |
| PEG 400 | 3.0 g |
| Ginkgo biloba extract, sold by Inverni | 0.3 g |
| Caffeine | 3.0 g |
| Sodium benzoate | 3.0 g |
| Preservative | 0.3 g |
| Perfume | 0.5 g |
| Ivy extract, sold by Gattefosse | 3.0 g |
| CARBOPOL 941 | 0.2 g |
| Isopropyl myristate | 1.0 g |
| Cetyl alcohol | 3.0 g |
| Stearic acid | 3.0 g |
| Glycerol monostearate | 3.0 g |
| Corn germ oil | 2.0 g |
| Demineralized water, sufficient amount for | 100.0 g |

EXAMPLE 3

A slimming water-in-oil emulsion

| | |
|---|---|
| "PROTEGIN X" | 20.0 g |
| Petrolatum oil | 10.0 g |
| Aromatic composition | 1.0 g |
| Turnsole oil | 15.0 g |
| Preservative | 0.3 g |
| Glycerol | 5.0 g |
| Magnesium sulfate | 0.5 g |
| Ivy extract, sold by Inverni | 0.5 g |
| "CETIOL HE" | 4.0 g |
| Ginkgo biloba extract, sold by Inverni | 1.0 g |
| Demineralized water, sufficient amount for | 100.0 g |

EXAMPLE 4

A slimming water-in-oil emulsion

| | |
|---|---|
| "ABIL WE 09" | 5.0 g |
| Isopropyl myristate | 5.0 g |
| "VOLATIL SILICONE 7158" | 8.0 g |
| Petrolatum oil | 5.0 g |
| "AEROSIL 200" | 0.4 g |
| Purcellin oil, sold by Dragocco | 14.0 g |
| Sodium chloride | 0.5 g |
| "TRANSCUTOL" | 3.0 g |
| Ginkgo biloba extract, sold by Beaufour | 0.5 g |
| Caffeine | 1.0 g |
| Escine acid, sold by Inverni | 0.5 g |
| Sodium hydroxide | 0.008 g |
| Preservative | 0.3 g |
| Demineralized water, sufficient amount for | 100.0 g |

EXAMPLE 5

A hydroalcoholic slimming gel

| | |
|---|---|
| "CARBOPOL 940" | 0.9 g |
| Ethyl alcohol | 20.0 g |
| Triethanolamine | 0.3 g |
| Perfume | 0.3 g |
| Preservative | 0.3 g |
| "TRANSCUTOL" | 5.0 g |
| Ivy extract, sold by Inverni | 1.0 g |
| Escine acid, sold by Inverni | 1.0 g |
| Ginkgo biloba extract, sold by Beaufour | 0.05 g |
| Sodium hydroxide | 0.015 g |
| Demineralized water, sufficient amount for | 100.0 g |

EXAMPLE 6

A slimming oil-in-water emulsion gel

| | |
|---|---|
| "CARBOPOL 940" | 0.6 g |
| "VOLATIL SILICONE 7158" | 3.0 g |
| Purcellin oil, sold by Dragocco | 7.0 g |
| "TEFOSE 63" | 3.0 g |
| Preservative | 0.3 g |
| Perfume | 0.4 g |
| Ethyl alcohol | 10.0 g |
| Triethanolamine | 0.2 g |
| Caffeine | 1.0 g |
| "CETIOL HE" | 2.0 g |
| Ginkgo biloba extract, sold by Beaufour | 0.8 g |
| Ivy extract, sold by Inverni | 0.5 g |
| Demineralized water, sufficient amount for | 100.0 g |

EXAMPLE 7

A slimming gel

| | |
|---|---|
| "CARBOPOL 940" | 0.6 g |
| "TRANSCUTOL" | 5.0 g |
| Triethanolamine | 0.3 g |
| Preservative | 0.3 g |
| Propylene glycol | 3.0 g |
| Ivy extract | 1.0 g |
| Escine acid | 0.5 g |
| Ginkgo biloba extract, sold by Inverni | 5 g |
| Sodium hydroxide | 0.007 g |
| Caffeine | 1.0 g |
| Demineralized water, sufficient amount for | 100.0 g |

EXAMPLE 8

A slimming gel with nonionic vesicles

| | |
|---|---|
| Polyglyceryl-3 cetyl ether | 3.8 g |
| β-sitosterol | 3.8 g |
| Dicetyphosphate | 0.4 g |
| Preservative | 0.3 g |
| Caffeine | 1.5 g |
| Ginkgo biloba extract, sold by Beaufour | 0.3 g |
| Sodium benzoate | 1.5 g |
| "TRANSCUTOL" | 3.0 g |
| Escine acid, sold by Inverni | 0.5 g |
| Sodium hydrochloride | 0.007 g |
| Ivy extract, sold by Gattefosse | 3.0 g |
| Turnsole oil | 35.0 g |
| Perfume | 0.6 g |
| "CARBOPOL 940" | 0.2 g |
| Triethanolamine | 0.2 g |
| Demineralized water, sufficient amount for | 100.0 g |

We claim:

1. A cosmetic slimming composition for topical application to the skin comprising in a cosmetic vehicle suitable for topical application to the skin, in combination, ginkgo biloba as an alpha-2-blocker present in an amount ranging from 0.2 to 5 weight percent based on the total weight of said composition and at least one other alpha-2-blocker selected from the group consisting of ivy present in an amount ranging from 0.01 to 15 weight percent based on the total weight of said composition and escine present in an amount ranging from 0.05 to 4 weight percent based on the total weight of said composition, or both.

2. The composition of claim 1 wherein said ginkgo biloba is present in an amount ranging from 0.05 to 2 weight percent based on the total weight of said composition.

3. The composition of claim 1 wherein said ivy is present in an amount ranging from 0.05 to 5 weight percent based on the total weight of said composition.

4. The composition of claim 1 wherein said escine is present in an amount ranging from 0.1 to 2 weight percent based on the total weight of said composition.

5. The composition of claim 1 which also contains at least one lipolytic agent acting at the level of phosphodiesterase.

6. The composition of claim 5 wherein said lipolytic agent is caffeine.

7. The composition of claim 1 which also contains at least one β-agonist.

8. The composition of claim 7 wherein said β-agonist is adrenalin or a derivative or analog thereof.

9. A cosmetic treatment for improving the esthetic appearance of a person comprising applying to the skin of said person the cosmetic slimming composition of claim 1.

10. The cosmetic treatment of claim 1 which is carried out in conjunction with a diet or an exercise program.

* * * * *